United States Patent [19]
Tiru et al.
[11] 4,149,852
[45] Apr. 17, 1979

[54] THERMOCHROMIC COMPOSITION, METHOD OF MAKING, AND USE

[75] Inventors: Mandayam O. Tiru; Maj-Britt I. Tiru, both of Jarfalla, Sweden

[73] Assignee: Kommanditbolaget Kockums Chemical AB & Co., Malmo, Sweden

[21] Appl. No.: 794,681

[22] Filed: May 6, 1977

[30] Foreign Application Priority Data

May 11, 1976 [SE] Sweden ............................... 7605338

[51] Int. Cl.[2] ............................................. G01K 11/06

[52] U.S. Cl. .................................... 23/230 R; 73/356; 116/207; 252/408; 422/58; 422/60

[58] Field of Search .......... 23/230 R, 253 TP, 253 R; 73/356; 116/114 V; 252/408

[56] References Cited

U.S. PATENT DOCUMENTS

| | | | |
|---|---|---|---|
| 2,195,395 | 4/1940 | Chapman | 116/114 V |
| 2,261,473 | 11/1941 | Jennings | 116/114 V |
| 2,614,430 | 10/1952 | Ballard et al. | 116/114 V |
| 2,809,116 | 10/1957 | Laskowski et al. | 73/356 UX |
| 3,935,834 | 2/1976 | Buhrmann, Jr. | 116/114 V |
| 3,977,945 | 8/1961 | Tornmarck | 426/88 X |

FOREIGN PATENT DOCUMENTS

| | | | |
|---|---|---|---|
| 3,977,945 | 8/1976 | United Kingdom | 73/356 |

OTHER PUBLICATIONS

Britton, "Hydrogen Ions Their Determination and Importance in Pure and Industrial Chemistry", D. Van Nostrand, Co., vol. 1, 1943, pp. 383 and 384.

*Primary Examiner*—Morris O. Wolk
*Assistant Examiner*—Arnold Turk
*Attorney, Agent, or Firm*—Beveridge, DeGrandi, Kline & Lunsford

[57] ABSTRACT pH indicator composition has controlled change of color at a selected sub-freezing temperature. The composition comprises at least one pH indicator, a buffer solution containing at least one inorganic ion in solution and a control agent or a precursor of a control agent. The buffer solution has a pH capable of changing when the temperature of the buffer solution is lowered to below freezing. The control agent is capable of effecting a change in ionic strength and proton composition of the frozen pH indicator composition to thereby control the temperature at which the color change occurs. A method of using the composition comprises lowering the temperature from a first temperature above freezing to a second temperature at which the pH indicator composition is in a substantially frozen state. The composition is particularly useful in a color change thermometer.

48 Claims, No Drawings

THERMOCHROMIC COMPOSITION, METHOD OF MAKING, AND USE

BACKGROUND OF THE INVENTION

This invention relates to a pH indicator composition having controlled change of color at a selected sub-freezing temperature. This invention also relates to a method of making and using the composition. Additionally, this invention relates to an article of manufacture comprising a casing containing the pH indicator composition of this invention. In a preferred embodiment, the article of manufacture is a color change thermometer.

It is generally recognized that pH indicators consist of an acid-base couple in which the acid has a color different from that of the base. These pH indicators are generally used to determine or at least give an idea of the pH value of a solution. A limitation of such pH indicators is that they cannot give an exact determination of the pH value, since they have a transition interval for the color change from acid to base form which amounts to about 1 to 2 pH units. The transition interval is also referred to by workers in the art as the indicator range or the color change interval, and is recognized as the range of pH values within which pronounced color change takes place. This transition interval is one reason why in recent years pH indicators have increasingly been replaced by electrical pH meters, which are capable of measuring the pH value of a solution more accurately. A still more serious limitation, which is common to both pH indicators and pH meters, is that they do not make it possible to measure the pH values of frozen solutions, i.e. substances that are in a solid state. The reason why pH indicators usually cannot be used to indicate the pH of a frozen solution is that the color of the pH indicator is not stable when the solution freezes. Rather, the color is prone to change.

Another problem which seemingly is not associated with the above-mentioned problem is that there has been no simple and efficient device available hitherto to permit visual indication, in a readily perceivable fashion, of temperature conditions, time-temperature conditions or temperature-space conditions, e.g. temperature distribution in a freezer compartment. For instance, in order to record the temperature in refrigerated boxes, freezers or freezer storage compartments, use has been made of conventional thermometers or temperature sensitive electrical means. These known devices for measuring the temperature, however, suffer from the drawback of sensing the temperature only at a single point or location in the compartment concerned. Consequently, a general picture of the temperature conditions prevailing in the compartment is not obtained. Moreover, the picture obtained may be misleading if the sensing means, as is often the case, is disposed in the coldest part of the compartment, such as adjacent to the supply opening for cooling air in a freezer compartment.

Thus, there has been a need in the art for a solution to the aforementioned problems. Specifically, there has been a need for a pH indicator composition, method of making the composition and method of using the composition applicable to frozen solutions. There has also been a need in the art for a method and means of measuring sub-freezing temperatures and for measuring time-temperature and temperature-space conditions, such as in a freezer compartment.

SUMMARY OF THE INVENTION

Accordingly, this invention aids in fulfilling these needs in the art. Specifically, this invention provides a pH indicator composition having controlled change of color at a selected sub-freezing temperature. The composition comprises at least one pH indicator in an amount sufficient to display a change of color upon change of pH. The composition also includes a buffer solution containing at least one inorganic ion in solution, wherein the buffer solution has a pH which is capable of changing when temperature of said buffer solution is lowered from a first temperature above the freezing point of said solution to a second temperature at which the solution is in a frozen state. Additionally, the composition includes a control agent or a precursor of a control agent, wherein the control agent is capable of effecting a change in ionic strength and proton composition of the frozen pH indicator composition to thereby cause, upon freezing, a change in pH of the pH indicator composition. The control agent is employed in an amount sufficient so that the pH indicator composition is capable of exhibiting a color at a selected temperature below freezing, which color is the same as the color of the pH indicator composition at a temperature above freezing. In a preferred embodiment, an aqueous buffer solution is employed.

This invention also provides the pH indicator composition of this invention in a frozen state.

Additionally, there is provided according to this invention a method of using the pH indicator composition of this invention. The method comprises lowering the temperature of the pH indicator composition from a first temperature above the freezing point of the composition to a second temperature at which the composition is in a substantially frozen state.

Also, this invention provides a method of preparing the pH indicator composition of this invention. The method comprises providing a buffer solution containing at least one inorganic ion in solution, wherein the buffer solution has a pH capable of changing when the temperature of the buffer solution is lowered from a first temperature above the freezing point of the solution to a second temperature at which the solution is in a frozen state. The pH indicator and the control agent or a precursor of the control agent are then added to the buffer solution to form the pH indicator composition of this invention. Again, the control agent is capable of effecting a change in ionic strength and proton composition of the frozen pH indicator composition to thereby cause, upon freezing, a change in pH of the pH indicator composition. The pH indicator is employed in an amount sufficient to display a change of color upon change of pH. The control agent is employed in an amount sufficient so that the pH indicator composition is capable of exhibiting a color at a selected temperature below freezing, which color is the same as the color of the indicator composition at a temperature above freezing.

There is also provided by this invention an article of manufacture comprising a sealed casing at least a portion of which is substantially translucent or transparent. The casing contains the pH indicator composition of this invention as a thermochromic composition. In a preferred embodiment, the article of manufacture of this invention is a temperature indicating device for use at sub-freezing temperatures. The temperature indicating device is particularly useful as a color change thermometer for use in freezer compartments.

DETAILED DESCRIPTION

As previously noted, the color of a pH indicator is not stable when a solution containing the indicator freezes. Rather, the indicator is prone to change color. This color change on freezing has been investigated and it has been discovered that it can occur from base color to acid color. Thus, if a solution at a temperature above freezing has a pH value close to or somewhat above the transition interval of the pH indicator (i.e., on the alkaline side of the transition interval), a color change from base color in the liquid solution to acid color in the frozen solution is obtained. A prerequisite for this color change on freezing is that the solution contains a substance that contributes not only to the ionic strength of the solution, but also to the proton composition of the solution. Such substances are typically inorganic buffers, such as phosphate buffers, and salts of organic acids. It is to be understood, however, that the reverse can occur, that is, a solution exhibiting acid color at a temperature above freezing can exhibit a base color when the solution is converted to a frozen state. This can occur, for example, in buffer systems comprised of a stronger base moiety than acid moiety. Such buffer systems can be formed of either a stronger base ion or a quantitatively larger amount of base ions than acid ions, e.g., an alkali salt of an organic acid, basic amino acids or other amines, amides or amino compounds. As used herein, the expression "proton composition" is the ratio of hydrogen ions to hydroxyl ions in the pH indicator composition.

Without limiting the present invention to any specific theory, it is believed that the above-described color change exhibited upon freezing a solution containing a pH indicator is due to the proton composition of the solution being radically changed upon freezing. This change is believed to be comprised of two parts. Firstly, the total conductivity is believed to be decreased upon freezing of the solution because the different ions in solution, including hydrogen ions and hydroxyl ions, substantially decrease in mobility. Secondly, for a system that becomes more acidic on freezing, the mobility or availability of hydroxyl ions is believed to decrease more than that of the hydrogen ions; that is, there is an apparent increase in the proton composition when the solution is frozen. This means that the frozen solution has an apparent lower or more acidic pH value than the solution in a liquid state. Since the color of a pH indicator depends on the ratio of hydrogen to hydroxyl ions (i.e., pH), the color condition of the pH indicator will thus change from base color to acid color, provided that the change in the proton composition is sufficient for the transition interval of the pH indicator to be passed when the solution freezes. It has been discovered that the change in the proton composition upon freezing generally corresponds to a shift in the pH value towards the acidic side of about 2 to 5 units depending upon the pH-indicator used. Thus, if a solution in liquid form is made more alkaline or already has a pH value about 2 to 5 units above the pK value of the pH indicator, the solution containing the indicator will not change color upon freezing.

The above-suggested explanation of the color change of a pH indicator upon freezing implies that the pH value of the solution shifts towards a more acidic value. Because the solution has to be made more alkaline to compensate for the decrease in pH on freezing, the pH in the solution is shifted towards a more alkaline value. This can be considered as a shift in the pK value (transition interval) of the pH indicator towards a more alkaline value because of the freezing, and this manner of viewing this phenomenon will be employed, inter alia, in the Examples hereinafter.

It has also been discovered that the color change of a pH indicator is mainly dependent upon the transition from liquid phase to solid phase only and to be substantially independent of the temperature. That is, when the color of the indicator has shifted because of freezing of the solution in which it is dissolved, no further color change occurs on subsequent lowering of the temperature below the freezing point.

It has also been discovered that the concentration of the substance (e.g., inorganic buffer or salt of an organic acid) in the solution, which contributes to the ionic strength and proton composition of the solution, has the effect that the higher the concentration of the substance (buffer) is in the solution, the more acidic the solution will be when it freezes.

The pH indicator composition of this invention is thermochromic. By this it is meant that the composition is capable of exhibiting a reversible change of color with change of temperature. More particularly, it is possible to control the change of color on freezing or at selected sub-freezing temperatures. This color change can be brought about in a predictable, reproducible and controllable manner.

The composition of this invention contains at least one pH indicator. Ordinarily only a single pH indicator will be used in the composition, but mixtures of indicators could also be employed. Any of the well-known indicators for measuring acidity of solutions can be employed in practicing this invention. Typical of suitable pH indicators are the following.

TABLE I

LIST OF TYPICAL INDICATORS

| Indicator | Transition Interval pH | Color Change |
|---|---|---|
| o-Cresol red (acid range) | 0.2–1.8 | Red-yellow |
| Thymol blue (acid range) | 1.2–2.8 | Red-yellow |
| Pentamethoxy red | 1.2–3.2 | Red violet-colorless |
| Tropeolin 00 | 1.3–3.2 | Red-yellow |
| 2,4-Dinitrophenol | 2.4–4.0 | Colorless-yellow |
| Methyl yellow | 2.9–4.0 | Red-yellow |
| Methyl orange | 3.1–4.4 | Red-orange |
| Bromophenol blue | 3.0–4.6 | Yellow-blue violet |
| Tetrabromophenol blue | 3.0–4.6 | Yellow-blue |
| Alizarin sodium sulfonate | 3.7–5.2 | Yellow-violet |
| x-Napthyl red | 3.7–5.0 | Red-yellow |
| p-Ethoxychrysoidine | 3.5–5.5 | Red-yellow |
| Bromocresol green | 4.0–5.6 | Yellow-blue |
| Methyl red | 4.4–6.2 | Red-yellow |
| Bromocresol purple | 5.2–6.8 | Yellow-purple |
| Chlorophenol red | 5.4–6.8 | Yellow-red |
| Bromothymol blue | 6.2–7.6 | Yellow-blue |
| p-Nitrophenol | 5.0–7.0 | Colorless-yellow |
| Azolitmin | 5.0–8.0 | Red-blue |
| Phenol red | 6.4–8.0 | Yellow-red |
| Neutral red | 6.8–8.0 | Red-yellow |

Many other suitable indicators are available to workers in the art. Other indicators and their properties can be found in the text by Roger G. Bates, *Determination of pH, Theory and Practice,* 2nd edition, John Wiley and Sons, New York (1973). Another excellent source from which suitable indicators can be selected is Bishop, *Indicators,* Pergamon Press Inc., New York (1972). The amount of the pH indicator employed in the pH indicator composition of this invention is, of course, sufficient to display a change of color upon change of pH. The amount to be employed can be determined from the aforementioned texts or with a minimum of experimentation. In general, 1 to 3 drops of a 0.1 to 0.5 percent aqueous indicator solution in each 10 ml of buffer solution is sufficient for pH measurements. Preferred pH indicators are set forth in the Examples hereinafter. Particularly preferred pH indicators are bromophenol red, chlorophenol red, and phenolphthalein.

The pH indicator composition of this invention also includes a buffer solution containing at least one inorganic ion in solution. The buffer solution has a pH, which is capable of changing when the temperature of the buffered solution is lowered from a first temperature above the freezing point of the solution to a second temperature at which the solution is in a frozen state. Ordinarily, the solvent medium for the buffer will be water. It is to be understood, however, that this invention is not limited to aqueous buffer solutions even though aqueous solutions are preferred. One can also employ non-aqueous solvents, such as aliphatic alcohols, for example, methanol, ethanol, and dodecanol. Other suitable solvents for the buffer are known in the art. Of course, mixed solvents and mixtures of aqueous and non-aqueous solvents can also be employed.

The buffer is comprised of a buffer pair having an acidic component and a basic component. Any of the well-known buffer systems can be employed in practicing this invention. The buffer employed in practicing this invention must be capable of giving at least one inorganic ion in the buffer solution. Thus, the buffer can be comprised of only inorganic ions or inorganic ions and organic radicals. Typical of the buffer substances that can be employed in practicing this invention are the following.

TABLE II

TYPICAL BUFFERS AND pH RANGES

| Acidic Component | Base Component | pH Range |
|---|---|---|
| HCl | Glycine | 1.0-3.7 |
| HCl | $Na_2H$ citrate | 1.0-5.0 |
| p-Toluenesulfonic acid | Na p-toluenesulfonate | 1.1-3.3 |
| KH sulfosalicylate | NaOH | 2.0-4.0 |
| HCl | KH phthalate | 2.2-4.0 |
| Citric acid | NaOH | 2.2-6.5 |
| Citric acid | $Na_2HPO_4$ | 2.2-8.0 |
| Furoic acid | Na furoate | 2.8-4.4 |
| Formic acid | NaOH | 2.8-4.6 |
| Succinic acid | Borax | 3.0-5.8 |
| Phenylacetic acid | Na phenylacetate | 3.4-5.1 |
| Acetic acid | Na acetate | 3.7-5.6 |
| KH phthalate | NaOH | 4.0-6.2 |
| NaH succinate | $Na_2$ succinate | 4.8-6.3 |
| $Na_2H$ citrate | NaOH | 5.0-6.3 |
| NaH maleate | NaOH | 5.2-6.8 |
| $KH_2PO_4$ | NaOH | 5.8-8.0 |
| $KH_2PO_4$ | Borax | 5.8-9.2 |
| $NaH_2PO_4$ | $Na_2HPO_4$ | 5.9-8.0 |
| HCl | Triethanolamine | 6.7-8.7 |
| HCl | Na diethylbarbiturate | 7.0-9.0 |
| Diethylbarbituric acid | Na diethylbarbiturate | 7.0-9.0 |
| $H_3BO_3$ or HCl | Borax | 7.0-9.2 |
| HCl | Tris(hydroxymethyl)-aminomethane | 7.2-9.0 |
| $H_3BO_3$ | NaOH | 8.0-10.0 |
| K p-phenolsulfonate | NaOH | 8.2-9.8 |
| Glycine | NaOH | 8.2-10.1 |
| $NH_4Cl$ | $NH_4OH$ | 8.3-9.2 |
| Glycine, $Na_2HPO_4$ | NaOH | 8.3-11.9 |
| HCl | Ethanolamine | 8.6-10.4 |
| Borax | NaOH | 9.2-11.0 |
| $NaHCO_3$ or HCl | $Na_2CO_3$ | 9.2-11.0 |
| Borax | $Na_2CO_3$ | 9.2-11.0 |

TABLE II-continued

TYPICAL BUFFERS AND pH RANGES

| Acidic Component | Base Component | pH Range |
|---|---|---|
| $Na_2HPO_4$ | NaOH | 11.0-12.0 |

Generally, the buffer solution employed in this invention is more acidic at a temperature below freezing than it is at a temperature above freezing. It will be understood, however, that one can also employ a buffer solution that is more alkaline at a temperature below freezing than it is at a temperature above freezing. Preferred buffers are set forth in the Examples hereinafter. A particularly preferred buffer is disodium hydrogen phosphate in aqueous solution.

The selection of a suitable buffer and the amount of the buffer pair in solution will depend upon the pH required, the buffer capacity of the buffer system, dilution effects and salt effects. Also, the chemical nature of the buffer material is such that substances added to the buffer will not form insoluble compounds or complexes or enter into other undesired side reactions with the medium. Directions for the preparation of suitable buffers of a particular pH are known in the art and available in prior art references.

Additionally, the composition of this invention includes a control agent or a precursor of a control agent. The control agent is capable of effecting a change in ionic strength and proton composition of the frozen pH indicator composition to thereby cause, upon freezing, a change in pH of the pH indicator composition. The control agent is employed in an amount sufficient so that the pH indicator composition is capable of exhibiting a color at a selected temperature below freezing, which color is the same as the color of the pH indicator composition at a temperature above freezing.

The control agent counteracts change in proton composition of the pH indicator composition due to freezing. It should be noted that the control agent need not itself change the proton composition. The important thing is that the effect of the control agent is such that the proton composition of the frozen solution is modified. This effect can be achieved by using various control agents which act, for instance, by changing the pH of the solution or by having a surfactant activity. It has been found that alcohols and carboxylic acids are particularly effective as control agents. By alcohols is meant organic compounds containing hydroxyl groups, and more particularly monovalent as well as polyvalent alcohols, e.g. methanol, ethanol, various glycols, glycerol and carbohydrates. The carboxylic acid control agents include organic compounds containing carboxyl groups, and more particularly mono-, di- and polycarboxylic acids. In addition to the "ordinary" aliphatic carboxylic acids, one can also employ aromatic carboxylic acids, keto acids, hydroxy acids and amino acids, including the amides, and salts of these acids.

In practice, the pure carboxylic acids are not employed as control agents as this would bring about an unwanted lowering of the pH of the solution. Rather, before the carboxylic acid control agent is added to the solution, the agent is adjusted to about the same pH as the solution, such as by the addition of NaOH. Thus, the carboxylic acid control agent substantially corresponds to a solution of free acid and its salt. Alternatively and preferably a salt of the acid, preferably an alkali metal, alkaline earth metal or ammonium salt, may be employed directly as a carboxylic acid control agent, and adjustment of pH made with an acid, such as HCl, or an alkali, such as NaOH.

It is also possible to employ a precursor of a control agent to effect the required change in ionic strength and proton composition. That is, one can also employ a material capable of producing a substance which changes the ionic strength and proton composition. An example of such a precursor substance is a mixture of an enzyme and a substrate for the enzyme. The action of the enzyme on the substrate produces the substances required as control agents. For instance, lipase-esterase/glyceryl tricapronate produces glycerol.

The exact mechanism by which the control agent operates has not been established. With glycerol, however, it is believed that this control agent works by its ability to attract water molecules possibly together with the pH indicator, which makes the pH indicator maintain its color. Furthermore, glycerol has a strong proton binding ability, which produces a decreased mobility or accessability of hydrogen ions as compared to hydroxyl ions. This results in an apparent more alkaline pH value. This shift of pH value towards a more alkaline value counteracts the shift of the pH value towards a more acidic value, which apparently occurs in the frozen solution without addition of control agent as explained earlier. Because of its proton binding ability, glycerol effects an apparent change in the pH value of the frozen solution towards a more alkaline value.

As to the carboxylic acid control agents employed in the present invention, they themselves bring about a real change in the conductivity, i.e. in the total conductivity as well as in the proton composition. The shift of the transition interval of the pH indicator on freezing may either be counteracted or further accentuated depending upon whether the carboxylic acid control agent cooperates with the particular buffer system or acts in opposition to the buffer system.

Typical of the aforementioned carbohydrates are saccharose, sorbitol and dextrose. Typical of the carboxylic acids are formic acid, acetic acid, succinic acid, citric acid and glutamic acid.

Disssociation of the control agent in the frozen state should alter the pH in the desired direction. For systems that become more acidic on freezing, one will usually employ a substance comprised of a strong alkali and weak acid. For systems that become more alkaline on freezing, one will employ a substance comprised of a weak alkali and a strong acid. Alcohols can be employed in either type of system.

The amount of control agent employed in practising this invention can also be expressed relative to the pK value of the pH indicator. It is known that a given pH indicator has a given pK value in a specific solvent medium. The pK value is a unitless number and the proton composition is also a unitless number. Thus, the amount of control agent required at freezing or at a given temperature below the freezing point of the pH indicator composition should be sufficient to bring about a change in the proton composition so that, for a pH indicator composition the pH of which becomes more acidic on freezing and passes below the pK value of the pH indicator, the proton composition is changed to a value less than that at the pK value of the indicator. On the other hand, for a pH indicator composition the pH of which becomes more alkaline on freezing, and passes above the pK value of the pH-indicator, the amount of control agent is such that the proton composition is changed to a value greater than that at the pK value of the indicator. In short, the function of the control agent is to adjust the pH of the composition of this invention especially in the frozen or solid state.

When using the aforementioned control agents, it has been discovered that they have the unexpected effect of making the color change of the pH indicator on freezing temperature dependent. That is, the color change does not need to occur in direct connection to the freezing, but can be made to occur at temperatures below the freezing point of the pH indicator composition. With the alcohol control agents, this is true when an inorganic buffer or salt of an organic acid is present. For the carboxylic acid control agents (including acid salts), on the other hand, it may also occur in the absence of an inorganic buffer; this is because the carboxylic acid plus alkali salt of a carboxylic acid themselves form a buffer system. Furthermore, it has been discovered that the temperature dependency of the color change of the pH indicator is dependent upon the concentration of the control agents added and on the initial pH of the buffer solution. Thus, an increasing concentration of control agent gives a decreasing temperature for color change at a constant pH.

On the other hand, a more alkaline initial pH of the buffer solution gives a decreasing temperature for the color change at a constant concentration of control agent.

As used herein, the term "freezing" means that the substance changes from a substantially liquid state to a substantially solid or slurry state. Freezing is to be distinguished from super-cooling, which can occur when the temperature of a composition is lowered. Super-cooling of the pH indicator composition of this invention can be avoided by adding substances in addition to the control agents. For example, the addition of small amounts of inorganic salts and other compounds that ionize readily in the buffer solution can be added to substantially prevent super-cooling. Such substances may also bring about a desirable change in ionic strength of the pH indicator composition. For example, one can employ salts of inorganic acids, such as salts of mineral acids. Typical of suitable compounds are potassium chloride, sodium chloride, ammonium sulfate, ammonium chloride, phosphates, sulfates, chlorides and nitrates, especially the alkali metal and ammonium salts thereof.

Also, preservatives can be added to the pH composition of this invention. Alcohols and glycerols are preferred for this purpose. These preservatives can also function as control agents in the pH indicator composition. A particularly preferred preservative is n-butanol, especially in a 2 percent (wt/vol) aqueous solution.

A typical formulation for a pH indicator composition according to this invention is as follows.

TABLE III

TYPICAL pH INDICATOR COMPOSITION

| Ingredient | Amount |
|---|---|
| $Na_2HPO_4 \cdot 2H_2O$ | 142.5g/2 l |
| Chlorophenol red 0.5% (wt/vol) | 4 l |
| Glycerol - 99.5% (wt/vol) | 350 ml |
| n-Butanol 2% (wt.vol) | 800 ml |
| Distilled water | to 40 l |

The pH of this solution is adjusted to 7.5 with 1M HCl. The resulting composition exhibits a color change at −18 degrees C. The typical formulation in Table III above can be converted into a pH indicator composition exhibiting a color change at −24 degrees C. by adding to 10 liters of the solution in Table III, 35.6 grams of disodium hydrogen phosphate dihydrate and 50 ml of 99.5 percent glycerol. The pH is adjusted, if necessary, to 7.96 to yield the composition exhibiting the color change at −24 degrees C.

This invention makes it possible to prepare articles of manufacture comprising the thermochromic composition of this invention in a sealed casing through which the change in color on freezing can be observed. Such an article of manufacture is especially well suited as a temperature indicating device for use at sub-freezing temperatures. This makes it possible to prepare a color change thermometer, which displays one color above the "transition temperature" (base color) and another color below the "transition temperature" (acid color), because of the fact that the color change of the pH indicator has been made temperature dependent. This color change can be made very distinct and perceptible. In fact, the color change thermometer can give clear information of such small temperature differences as 1 to 2 degrees centigrade.

By filling an elongated tube with the thermochromic composition of this invention, there is thus provided an elongated color thermometer that can be mounted on the wall in a cooling or freezing room or compartment, whereby the color change thermometer will indicate the level in the room or compartment at which the temperature is acceptable and the level in the room or compartment at which the temperature is too high.

The casing for the thermochromic composition is substantially translucent or substantially transparent. Preferably, at least a portion of the casing is substantially clear. Preferably, the casing should be comprised of a material that is substantially impermeable to moisture at the operating temperatures of the color change thermometer, such as between about 25 degrees C. and −90 degrees C. Use of such moisture impermeable materials extends the life of the color change thermometer, since the liquids in the thermochromic composition are not permitted to escape. Of course, loss of liquid in the thermochromic composition would change the properties of the composition and possibly the temperature at which the color change occurs. This is to be avoided.

Typical of the suitable materials for the casing are vitreous glasses, ceramics, glass-ceramics, thermoplastic and thermosetting materials. The choice of the casing material is dependent upon the conditions to which the material will be subjected. Factors such as ease of fabrication and economy are also important for widespread commercial application. Thermoplastic materials are preferred because of their ease of fabrication and ready availability. Such materials include polyvinyl chloride, polyethylene, polypropylene, polytetrafluoroethylene, polychlorotrifluoroethylene and acrylic polymers. There are many other thermoplastic materials commercially available that can be readily employed. Metal casings can also be employed, provided that they are equipped with a viewing port through which the color change of the thermochromic composition can be observed. Metal casings may find application where rapid heat transfer is required. The rate of heat transfer can also be increased by increasing the surface-to-volume ratio of the color change thermometer, such as by providing the thermometer with a rectilinear, oval or similar cross-section. Where chemical resistance is important, the casing can be comprised of chemically resistant materials, such as polycarbonates, polytetrafluoroethylene, polychlorotrifluoroethylene, polychloroprene, chlorosulfonated polyethylene or epoxy compounds. Not only does the shape of the casing affect the heat transfer characteristics of the color change thermometer, but is has also been found that a larger amount of pH indicator is required for a thinner thermometer than for a thicker thermometer.

It will be understood that either a flexible or rigid casing can be employed. In one embodiment of this invention, the casing is a substantially moisture impermeable, flexible, elongated tube comprised of a thermoplastic material. The casing is mounted on a substantially rigid frame, such as a piece of sheet metal, which serves to support the flexible tube. The flexible tube makes it relatively easy to fabricate the thermometer, while the rigid frame provides adequate support during use of the thermometer.

Instead of filling the thermochromic composition of this invention into an elongated tube, one can also produce an elongated strip having regularly spaced chambers, each chamber filled with the thermochromic composition. This embodiment is more practical than the embodiment comprising a single elongated tube, because the strip can easily be severed between the chambers to produce stripped portions of the desired length. Fabrication of the color change thermometer is thereby facilitated.

In another embodiment of this invention, the color change thermometer can be employed to indicate temperatures within a preselected range. This is achieved by providing a casing comprised of a multiplicity of discrete chambers. Each chamber is filled with a thermochromic composition, such that the change of color exhibited by the contents of each chamber occurs at a selected sub-freezing temperature that is different from the sub-freezing temperature at which the contents of any other chamber exhibits a color change. In short, the chambers are filled with different thermochromic compositions showing color changes at different temperatures below the freezing point. In this way, a thermometer is produced, which by way of its color, displays the prevailing temperature in an easily perceptible and visually distinct way.

In another application of the color change thermometer of this invention, a single chamber or capsule is filled with the thermochromic composition of this invention, which gives a color change at a certain desired temperature, e.g. −18 degrees C. The single chamber or capsule is attached to a frozen food product. At each instance during the handling of the frozen food product, the capsule enclosing the thermochromic composition will show if the temperature is above or below the chosen temperature (e.g. −18 degrees C.).

It will be understood that each separate color change thermometer gives an indication of color change only at a particular temperature, which is characteristic of the combination of pH indicator, buffer solution, pH value and the nature and amount of the control agent. By suitably combining these factors, however, it is possible to provide color change thermometers capable of displaying a color change at any sub-freezing temperature.

This invention will be more fully understood by reference to the following Examples in which all parts and proportions are by weight unless otherwise indicated. Percentages are expressed on a weight per volume basis, e.g. grams per ml. In all of the Examples, the concentration of pH indicator was 0.025 percent.

EXAMPLE 1—Effect of Temperature on Color Change

This Example illustrates the change of color that occurs when solutions containing nitrazine yellow or bromothymol blue as pH indicators are frozen.

A first set of eleven containers was prepared by filling each container with an aqueous buffer solution of 0.02 M $Na_2HPO_4$. The buffer solution had a pH of 9.4. Then nitrazine yellow was added to each container. The pH value of the solution in each container was adjusted with 1 N HCl so that a range of pH values from 9.40 to 4.60 was obtained.

A second set of eleven containers was prepared in the same way. The first set of containers was maintained at +20° C., but the second set was frozen at −20° C. The results are reported in Table 1. It will be apparent that the difference in color between the frozen and unfrozen states is significantly affected by temperature.

This procedure was repeated, except that bromothymol blue was employed instead of nitrazine yellow. Similar results were obtained and are also reported in Table 1. As will clearly appear from Table 1, both nitrazine yellow and bromothymol blue in a solution, which is buffered with the inorganic buffer $Na_2HPO_4$, indicate a shift of the transition interval when freezing is effected.

Comparative Test

By way of comparison, corresponding tests were carried out involving, however, indicator solutions that were buffered with 0.02 M of the organic buffer tris-hydroxymethyl aminomethane (Tris). Here, no appreciable shift of the transition interval was obtained. This is because Tris is a substantially non-dissociated organic compound that contributes only insignificantly to the proton composition.

In order to demonstrate that it is not the degree of dissociation of ions that is of importance whether or not the transition interval is to shift, tests were also carried out using indicator solutions that were buffered with Tris-buffers and to which had been added NaCl, i.e. a substance changing only the ionic strength but not the proton composition. As is apparent from Table 1, no appreciable shift of the transition interval was obtained in this instance either. Thus, it is important to control both ionic strength and proton composition.

TABLE 1

| | 0.02 M $Na_2HPO_4$ buffer | | | |
|---|---|---|---|---|
| pH (+20° C.) | Nitrazine yellow color at +20° C. | −20° C. | Bromothymol blue color at +20° C. | −20° C. |
| 9.40 | dark violet | | blue | yellow |
| 9.00 | dark violet | greenish brown | blue | yellow |
| 8.50 | dark violet | yellowish red | blue | yellow |
| 8.00 | dark violet | yellowish-red | blue | yellow |
| 7.50 | dark violet | yellowish-red | bluish green | yellow |
| 7.00 | violet | yellowish-red | green | yellow |
| 6.50 | brown | yellowish-red | green | yellow |
| 6.00 | brownish red | yellowish-red | yellowish green | yellow |
| 5.50 | reddish yellow | yellowish-red | yellow | yellow |
| 5.00 | yellowish red | yellowish-red | yellow | yellow |
| 4.60 | yellowish red | yellowish-red | yellow | yellow |
| | | 0.02 M Tris-buffer | | |
| 9.40 | dark violet | dark violet | blue | blue |
| 9.00 | dark violet | dark violet | blue | blue |
| 8.50 | dark violet | dark violet | blue | bluish green |
| 8.00 | dark violet | dark violet | blue | green |
| 7.50 | dark violet | dark violet | bluish green | greenish yellow |
| 7.00 | violet | violet | green | yellow |
| 6.50 | brown | light violet | green | yellow |
| 6.00 | brownish red | yellowish brown | yellowish green | yellow |
| 5.50 | reddish yellow | yellowish red | yellow | yellow |
| 5.00 | yellowish red | yellowish red | yellow | yellow |
| 4.60 | yellowish red | yellowish red | yellow | yellow |
| | | 0.02 M Tris-buffer + 0.1 M NaCl | | |
| pH (+20° C.) | Nitrazine yellow color at +20° C. | −18° C. | Bromothymol blue color at +20° C. | −20° C. |
| 9.4 | violet | violet | blue | light blue |
| 9.0 | violet | violet | blue | light blue |
| 8.5 | violet | violet | blue | light blue |
| 8.0 | violet | violet | blue | light blue |
| 7.5 | violet | violet | greenish blue | reddish grey |
| 7.0 | light violet | violet | green | greyish green |
| 6.5 | lilac brown | violet | green | yellowish green |
| 6.0 | brown | light brown | yellowish green | yellow |
| 5.5 | — | — | yellow | yellow |
| 5.0 | yellow | yellowish red | yellow | yellow |

EXAMPLE 2—Temperature Effect on Different Indicators

In a manner similar to Example 1, tests were carried out using a large number of different pH indicators. It was found that all of them displayed a shift of the transition interval on freezing. Table 2 is a compilation of the different pH indicators tested, their normal transition intervals at +20° C. (solid lines) and at −20° C. (broken lines). In all instances, the indicator solutions were buffered with 0.02 M $Na_2HPO_4$. The pH was adjusted with 1 M HCl or 1 M NaOH.

EXAMPLE 3—Effect of Glycerol as a Control Agent

In this Example, tests were conducted involving the addition of glycerol to different pH indicator solutions that were buffered with phosphate buffers, as described above. The measurements were effected at +20° C. and at −18° C., the pH value being maintained constant at 7.0. All samples were frozen at −18° C. The results appear in Table 3. Columns 2 through 7 indicate the color at −18° C. Column 8 indicates the color at +20° C. It should be pointed out that the indicated glycerol concentrations refer to a 87% glycerol solution in water.

It will be apparent from Table 3 that there was a color change for each indicator when the indicator solution was frozen and no control agent was employed. (compare columns 7 and 8). Columns 2 through 6 indicate, however, that a control agent can be employed to regulate whether a color change occurs on freezing (compare, e.g., columns 4, 5 and 6 with column 8 for congo red). The Table also indicates that when a color change on freezing occurs with a control agent, the color may be affected by the control agent.

Table 2

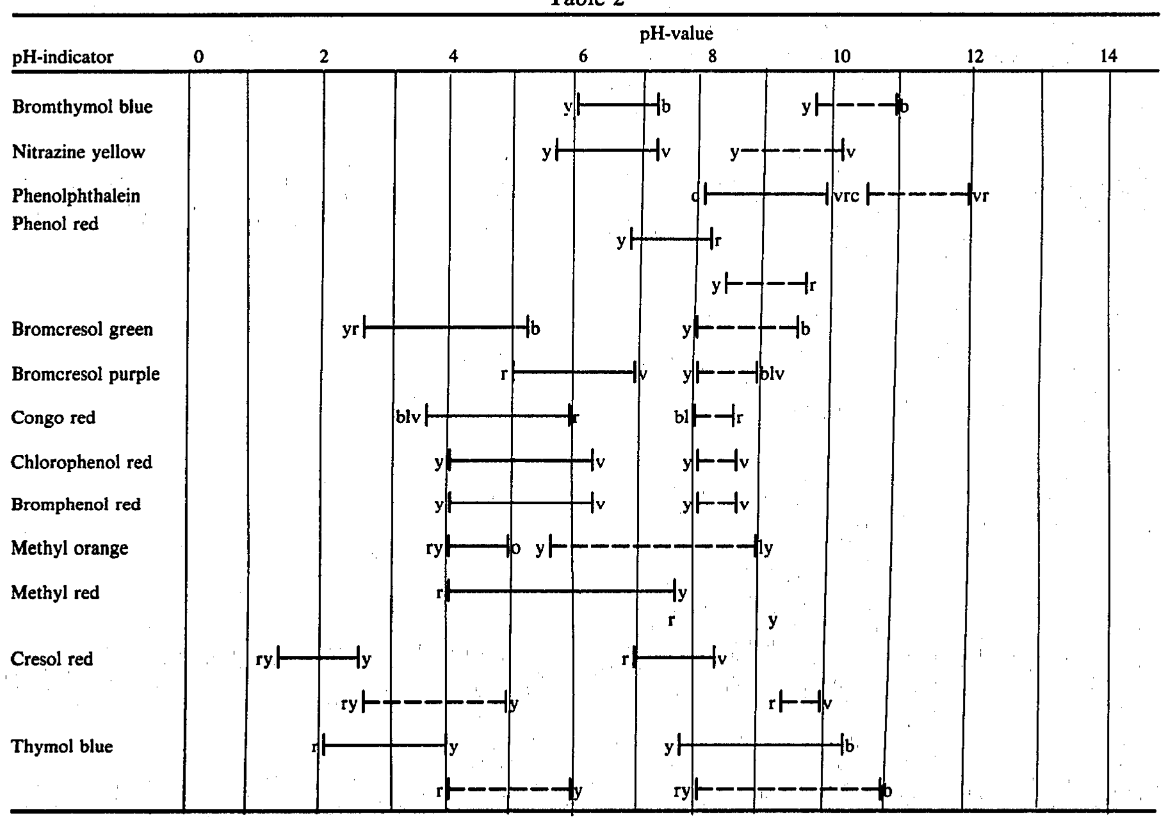

b=blue
bl=black
blv=blackish violet
br=brown
c=colourless
grbr=greyish brown
ly=light yellow
lbr=light brown
o=orange
r=red
ry=reddish yellow
y=yellow
yr=yellowish red
v=violet
vr=violet red Table 3

| Glyerol Content pH-indicator | 1% | 2% | 5% | 10% | 20% | 0% = check | Color at 20° C. |
|---|---|---|---|---|---|---|---|
| Chlorophenol red | yellow tinted with red | red | red | red | red | yellow | violet |
| Bromcresol green | bluish green | bluish green | blue | blue | blue | green | blue |
| Congo red | brownish red | dark red | red | red | red | black | red |

EXAMPLE 4—Effect of pH, Temperature and Control Agent on Bromocresol Green

This Example shows the effect of pH, temperature and glycerol (87% in water) content on the color change of bromocresol green. The indicator solution contained, as above, 0.02 M $Na_2HPO_4$. The results appear in Table 4. The results in Table 4 can be compared with the results in Table 3 in which only a single sub-freezing temperature was employed. Also, comparing column 2 of Table 4 with column 4 of Table 4, it will be apparent that, for bromocresol green, the lower the pH, the higher the sub-freezing temperature at which a color change occurs.

EXAMPLE 5—Chlorophenol Red

This Example shows the effect of pH, temperature and glycerol content on the color change of chlorophenol red. The indicator solution contained, as above, 0.02 M $Na_2HPO_4$. The results appear in Table 5. The glycerol was 87% in water.

EXAMPLE 6—Effect of Different Control Agents

This Example illustrates the color-change counteracting effect of different control agents according to the invention. The indicator solutions consisted, respectively, of chlorophenol red and bromocresol green in aqueous solution buffered with 0.02 M $Na_2HPO_4$. The pH values of the solutions were adjusted with HCl to 6.0–6.5. The results appear in Table 6.

EXAMPLE 7—Effect of Different Sub-Freezing Temperatures

This test demonstrates (a) the shift of the transition interval in a pH indicator (Congo red) on freezing; and (b) that this shift does not continue upon continued temperature reduction below freezing point, i.e. as long as the indicator composition is in either the liquid or the solid phase, the transition interval remains independent of temperature, provided no control agent according to the invention, e.g. glycerol, has been added. The results appear in Table 7.

Table 4

| Temperature ° C. | pH 4.0 0.5% glycerol | pH 5.0 1.0% glycerol | pH 6.0 0.5% glycerol |
|---|---|---|---|
| −14 | Bluish green | Bluish green | Bluish green |
| −16 | Yellow | Greenish yellow | Yellowish green |
| −18 | Yellow | Yellowish green | Yellowish green |
| −20 | Yellow | Yellowish green | Yellow |
| −22 | Yellow | Yellow | Yellow |

Table 5

| Temperature ° C. | pH 5.0 1.0% glycerol | pH 5.5 0.5% glycerol | pH 6.0 0.5% glycerol |
|---|---|---|---|
| −14° | Violet | Violet | Violet |
| −16° | Yellowish red | Red | Yellow |
| −18° | Yellowish red | Yellow | Yellow |
| −20° | Yellow | Yellow | Yellow |

Table 5-continued

| Temperature ° C. | pH 5.0 1.0% glycerol | pH 5.5 0.5% glycerol | pH 6.0 0.5% glycerol |
|---|---|---|---|
| −22° | Yellow | Yellow | Yellow |

Table 6

| Control agent (weight/volume %) | Chlorophenol red +20° C. | Chlorophenol red −18° C. | Bromcresol green +20° C. | Bromcresol green −18° C. |
|---|---|---|---|---|
| 0 = Check (only phosphate buffer) | Red | Yellow | Blue | Yellow |
| Dextrose (5%) | Red | Yellowish red | Blue | Yellowish green |
| Sorbitol (5%) | Red | Yellowish red | Blue | Yellowish green |
| Saccharose (5%) | Red | Yellowish red | Blue | Greenish yellow |
| Tween 80 (surfactant containing polyoxyethylene (20) sorbitan monooleate (10%) | Reddish yellow | Yellowish red | Green | Green |
| Glycerol (8.7%) | Red | Red | Blue | Blue |
| Ethylene glycol (10%) | Red | Red | Blue | Blue |
| Polyethylene glycol (5%) | Red | Red | Bluish green | Blue |
| Cellosolve (5%) | Red | Red | Bluish green | Blue |
| Methanol (5%) | Red | Yellowish red | Bluish green | Green |
| Ethanol (5%) | Red | Yellowish red | Bluish green | Blue |
| Sodium glutamate (5%) | Red | Red | Bluish green | Blue |
| Sodium succinate (5%) | Red | Yellowish red | Bluish green | Green |
| Sodium acetate (5%) | Red | Red | Bluish green | Light green |
| Sodium citrate (5%) | Red | Red | Bluish green | Green |
| Ammonium formate (5%) | Red | Red | Bluish green | Blue |

Table 7

The color of a Congo-red indicator in an aqueous solution buffered with 0.02 M $Na_2HPO_4$.

| pH (+20° C.) | −20° C. | −15° C. | −6° C. | +5° C. | +10° C. | +20° C. |
|---|---|---|---|---|---|---|
| 9.9 | red | red | red | red | red | red |
| 9.15 | red | red | red | red | red | red |
| 8.5 | red | red | reddish brown | red | red | red |
| 8.0 | black | black | black | red | red | red |
| 7.5 | black | black | black | red | red | red |
| 7.0 | black | black | black | red | red | red |
| 6.5 | black | black | black | red | red | red |
| 6.0 | black | black | black | red | red | red |
| | Frozen | | | | Liquid | |

EXAMPLE 8—Effect of Carboxylic Acid Control Agent

In order to demonstrate that the carboxylic acid control agents according to the invention may cause the transition interval of the pH indicator to be temperature-dependent in the frozen system also in the absence of a buffer, tests were carried out using a solution containing 5% of sodium succinate (carboxylic acid control agent), and chlorophenol red as pH indicator. The color of the indicator was observed at +20° C. as well as at three different temperatures below freezing point, the results being as follows:

Table 8

| Temperature (° C.) | Color |
|---|---|
| +20 | red |
| − 6 | red |
| −10 | yellowish red |
| −18 | yellowish red |

The color change occurring between −6° C. and −10° C. is indicative of a change of the transition interval of the pH indicator.

EXAMPLE 9—Control Agent Precursor

Table 9 shows various examples of enzyme-substrate-combinations, which are precursors to the desired control agent, and which by enzymatic reaction produce the desired control agent. It is to be understood that the combinations shown in Table 9 comprise a few illustrative examples only, and that one skilled in the art can select many other enzyme-substrate-combinations, which by enzymatic reaction, produce the control agent.

Table 9

| Enzyme | Substrate | Control Agent | Other Products |
|---|---|---|---|
| Phosphatase | Glucose-6-phosphate | Glucose | Phosphate |
| Phosphatase | β-glycerophosphate | Glycerol | Phosphate |
| Esterase | Ethyl Butyrate | Ethanol | Butyrate |
| Lipase | Triglyceride | Glycerol | Salt of fatty acid |

Of course, the medium employed for the buffer solution must be a solvent for the pH indicator, the buffer pair and the control agent. The amount of indicator employed in the pH indicator composition of this invention will preferably be about 0.01 to about 0.05 percent (wt/vol). The term "thermochromic composition" and the term "pH indicator composition" are used interchangeably herein to identify the composition of this invention.

What is claimed is:

1. A pH indicator composition having controlled reversible change of color at a selected sub-freezing temperature, said composition comprising:

(A) at least one pH indicator in an amount sufficient to display a change of color upon change of pH;

(B) a buffer solution containing at least one inorganic ion in solution, wherein said buffer solution has a pH which is capable of changing when temperature of said buffer solution is lowered from a first temperature above the freezing point of said solution to a second temperature at which said solution is in a frozen state; and (C) a control agent or a precursor of a control agent, wherein said control agent is capable of effecting a change in ionic strength and proton composition of said pH indicator composition when frozen to thereby cause, upon freezing, a shift in change in pH of said pH indicator composition from that due to the pH change of said buffer solution;

and wherein said control agent is in an amount sufficient to that said pH indicator composition is capable of exhibiting a color at a selected temperature below freezing, which color is the same as the color of said pH indicator composition at a temperature above freezing.

2. Composition according to claim 1 wherein said buffer solution contains a buffer pair capable of dissociating into organic and inorganic ions.

3. Composition according to claim 1 wherein said control agent is selected from the group consisting of alcohols, carboxylic acids and precursor substances therefor.

4. Composition according to claim 1 wherein said precursor of said control agent is capable of yielding an alcohol or a carboxylic acid in said pH indicator composition.

5. Composition according to claim 1 wherein said buffer solution is more acidic at said second temperature than at said first temperature.

6. Composition according to claim 1 wherein said buffer solution is more alkaline at said second temperature than at said first temperature.

7. Composition according to claim 1 wherein said pH indicator composition contains (D) an inorganic salt capable of dissociating in said buffer solution to thereby change the ionic strength of said solution.

8. A method of using the pH indicator composition of claim 1 comprising lowering the temperature of said pH indicator composition from a first temperature above the freezing point of said pH indicator composition to a second temperature at which said pH indicator composition is in frozen state.

9. Composition according to claim 1 wherein said change of color occurs at a selected sub-freezing temperature to about −90° C.

10. Composition according to claim 1 wherein said buffer solution is comprised of a buffer pair in solution in a solvent selected from the group consisting of water, an aliphatic alcohol or mixtures thereof.

11. Composition according to claim 10 wherein said aliphatic alcohol is selected from the group consisting of methanol, ethanol and dodecanol.

12. A pH indicator composition having controlled reversible change of color at a selected sub-freezing temperature, said composition comprising:

(A) at least one pH indicator in an amount sufficient to display a change of color upon change of pH;

(B) an aqueous buffer solution containing at least one inorganic ion in solution, wherein said buffer solution has a pH which is capable of changing when temperature of said buffer solution is lowered from a first temperature above the freezing point of said solution to a second temperature at which said solution is in a frozen state; and (C) a control agent or a precursor of a control agent, wherein said control agent is capable of effecting a change in ionic strength and proton composition of said pH indicator composition when frozen to thereby cause, upon freezing, a shift in change in pH of said pH indicator composition from that due to the pH change of said buffer solution;

and wherein said control agent is in an amount sufficient so that said pH indicator composition is capable of exhibiting a color at a selected temperature below freezing, which color is the same as the color of said pH indicator composition at a temperature above freezing.

13. Composition according to claim 12 wherein said buffer solution contains a buffer pair capable of dissociating into organic and inorganic ions.

14. Composition according to claim 12 wherein said buffer solution is more acidic at said second temperature than at said first temperature.

15. Composition according to claim 12 wherein said buffer solution is more alkaline at said second temperature than at said first temperature.

16. A method of using the pH indicator composition of claim 12 comprising lowering the temperature of said pH indicator composition from a first temperature above the freezing point of said pH indicator composition to a second temperature at which said pH indicator composition is in a frozen state.

17. Composition according to claim 12 wherein said pH indicator composition contains (D) an inorganic salt capable of dissociating in said buffer solution to thereby change the ionic strength of said solution.

18. Composition according to claim 17 wherein said inorganic salt is a salt of a strong mineral acid.

19. Composition according to claim 12 wherein said control agent is selected from the group consisting of alcohols, carboxylic acids and precursor substances therefor.

20. Composition according to claim 19 wherein said alcohol contains at least one hydroxyl group and is selected from the group consisting of methanol, ethanol, glycols, glycerol and carbohydrates.

21. Composition according to claim 20 wherein said carbohydrate is selected from the group consisting of saccharose, sorbitol and dextrose.

22. Composition according to claim 19 wherein said carboxylic acid contains at least one carboxyl group and is selected from the group consisting of aliphatic and aromatic carboxylic acids, keto acids, hydroxy acids and amino acids.

23. Composition according to claim 22 wherein said carboxylic acid is selected from the group consisting of formic acid, acetic acid, succinic acid, citric acid and glutamic acid.

24. Composition according to claim 19 wherein said precursor substance is a salt of a carboxylic acid or a mixture of an enzyme and a substrate for said enzyme, which mixture is capable of producing the control agent by enzymatic reaction.

25. Composition according to claim 24 wherein said precursor substance is lipase-esterase/glyceryl tricapronate.

26. A pH indicator composition having controlled reversible change of color at a selected sub-freezing temperature to about −90° C., said composition comprising:

(A) at least one pH indicator in an amount sufficient to display a change of color upon change of pH;

(B) an aqueous buffer solution containing at least one inorganic ion in solution, wherein said buffer solution has a pH which is capable of changing when temperature of said buffer solution is lowered from a first temperature above the freezing point of said solution to a second temperature at which said solution is in a frozen state; and (C) a control agent selected from the group consisting of alcohols, carboxylic acids and precursor substances thereof, wherein said control agent is capable of effecting a change in ionic strength and proton composition of said pH indicator composition when frozen to thereby cause, upon freezing, a shift in change in pH of said pH indicator composition from that due to the pH change of said buffer solution;

and wherein said pH indicator has a pK value in said pH indicator composition and said control agent is in an effective amount to cause a change in said proton composition so that:

(a) for a pH indicator composition, which becomes more acidic on freezing, said proton composition is changed to a value less than that at said pK value; and (b) for a pH indicator composition, which becomes more alkaline on freezing, said proton composition is changed to a value greater than that at said pK value.

27. A method of using the pH indicator composition of claim 26 comprising lowering the temperature of said pH indicator composition from a first temperature above the freezing point of said pH indicator composition to a second temperature at which said pH indicator composition is in a frozen state.

28. A pH indicator composition in a frozen state, said composition having controlled reversible change of color at a selected sub-freezing temperature, said composition comprising:

(A) at least one pH indicator in an amount sufficient to display a change of color upon change of pH;

(B) a buffer solution containing at least one inorganic ion in solution, wherein said buffer solution has a pH which is capable of changing when temperature of said buffer solution is lowered from a first temperature above the freezing point of said solution to a second temperature at which said solution is in a frozen state; and (C) a control agent or a precursor of a control agent, wherein said control agent is capable of effecting a change in ionic strength and proton composition of said pH indicator composition when frozen to thereby cause, upon freezing, a shift in change in pH of said pH indicator composition from that due to the pH change of said buffer solution;

and wherein said control agent is in an amount sufficient so that said pH indicator composition is capable of exhibiting a color at a selected temperature below freezing, which color is the same as the color of said pH indicator composition at a temperature above freezing.

29. A pH indicator composition in a frozen state, said composition having controlled reversible change of color at a selected sub-freezing temperature, said composition comprising:

(A) at least one pH indicator in an amount sufficient to display a change of color upon change of pH;

(B) an aqueous buffer solution containing at least one inorganic ion in solution, wherein said buffer solution has a pH which is capable of changing when temperature of said buffer solution is lowered from a first temperature above the freezing point of said solution to a second temperature at which said solution is in a frozen state; and (C) a control agent or a precursor of a control agent, wherein said control agent is capable of effecting a change in ionic strength and proton composition of said pH indicator composition when frozen to thereby cause, upon freezing, a shift in change in pH of said pH indicator composition from that due to the pH change of said buffer solution;

and wherein said control agent is in an amount sufficient so that said pH indicator composition is capable of exhibiting a color at a selected temperature below freezing, which color is the same as the color of said pH indicator composition at a temperature above freezing.

30. A pH indicator composition in a frozen state, said composition having controlled reversible change of color at a selected sub-freezing temperature, said composition comprising:

(A) at least one pH indicator in an amount sufficient to display a change of color upon change of pH;

(B) an aqueous buffer solution containing at least one inorganic ion in solution, wherein said buffer solution has a pH which is capable of changing when temperature of said buffer solution is lowered from a first temperature above the freezing point of said solution to a second temperature at which said solution is in a frozen state; and (C) a control agent or a precursor of a control agent, wherein said control agent is capable of effecting a change in ionic strength and proton composition of said pH indicator composition when frozen to thereby cause, upon freezing, a shift in change in pH of said pH indicator composition from that due to the pH change of said buffer solution;

and wherein said pH indicator has a pK value in said pH indicator composition and said control agent is in an effective amount to cause a change in said proton composition so that:

(1) for a pH indicator composition which becomes more acidic on freezing, said proton composition is changed to a value less than that at said pK value; and (2) for a pH indicator composition which becomes more alkaline on freezing, said proton composition is changed to a value greater than that at said pK value.

31. A method of preparing a pH indicator composition having controlled reversible change of color at a selected sub-freezing temperature, said method comprising:

I. providing (A) a buffer solution containing at least one inorganic ion in solution, wherein said buffer solution has a pH which is capable of changing when temperature of said buffer solution is lowered from a first temperature above the freezing point of said solution to a second temperature at which said solution is in a frozen state; and II. adding to said buffer solution (2) a control agent or a precursor of a control agent, wherein said control agent is capable of effecting a change in ionic strength and proton composition of said pH indicator composition when frozen to thereby cause, upon freezing, a shift in change in pH of said pH indicator composition from that due to the pH change of said buffer solution; and (C) at least one pH indicator in an amount sufficient to display a change of color upon change of pH;

wherein said control agent is in an amount sufficient so that said pH indicator composition is capable of exhibiting a color at a selected temperature below freezing, which color is the same as the color of said pH indicator composition at a temperature above freezing.

32. A method as claimed in claim 31 comprising adding as a control agent a carboxylic acid containing at least one carboxyl group and selected from the group consisting of aliphatic and aromatic carboxylic acids, keto acids, hydroxy acids and amino acids.

33. A method as claimed in claim 32 in which said carboxylic acid is selected from the group consisting of formic acid, acetic acid, succinic acid, citric acid and glutamic acid.

34. A method as claimed in claim 31 in which said precursor of a control agent is an enzyme-substrate mixture, which produces the control agent by enzymatic reaction.

35. A method as claimed in claim 34 in which said enzyme-substrate mixture is lipase-esterase-glyceryl tricapronate.

36. A method as claimed in claim 31 comprising adding as control agent a substance selected from the group consisting of alcohols, carboxylic acids and precursor substances therefor.

37. A method as claimed in claim 36 in which said alcohol contains at least one hydroxyl group and is selected from the group consisting of methanol, ethanol, glycols, glycerol and carbohydrates.

38. A method as claimed in claim 37 in which said carbohydrate is selected from the group consisting of saccharose, sorbitol and dextrose.

39. A method of preparing a pH indicator composition having controlled reversible change of color at a selected sub-freezing temperature, said method comprising mixing:

(A) at least one pH indicator in an amount sufficient to display a change of color upon change of pH;

(B) an aqueous buffer solution containing at least one inorganic ion in solution, wherein said buffer solution has a pH which is capable of changing when temperaure of said buffer solution is lowered from a first temperature above the freezing point of said solution to a second temperature at which said solution is in a frozen state; and (C) a control agent or a precursor of a control agent, wherein said control agent is capable of effecting a change in ionic strength and proton composition of said pH indicator composition when frozen to thereby cause, upon freezing, a shift in change in pH of said pH indicator composition from that due to the pH change of said buffer solution;

and wherein said pH indicator has a pK value in said pH indicator composition and said control agent is in an effective amount to cause a change in said proton composition so that:

(a) for a pH indicator composition which becomes more acidic on freezing, said proton composition is changed to a value less than that at said pK value; and (b) for a pH indicator composition which becomes more alkaline on freezing, said proton composition is changed to a value greater than that at said pK value.

40. An article of manufacture comprising a sealed casing at least a portion of which is substantially translucent or transparent, said casing containing a thermochromic composition having controlled reversible change of color at a selected sub-freezing temperature, said composition comprising:

(A) at least one pH indicator in an amount sufficient to display a change of color upon change of pH;

(B) a buffer solution containing at least one inorganic ion in solution, wherein said buffer solution has a pH which is capable of changing when temperature of said buffer solution is lowered from a first temperature above the freezing point of said solution to a second temperature at which said solution is in a frozen state; and (C) a control agent or a precursor of a control agent, wherein said control agent is capable of effecting a change in ionic strength and proton composition of said pH indicator composition when frozen to thereby cause, upon freezing, a shift in change in pH of said pH indicator composition from that due to the pH change of said buffer solution;

and wherein said control agent is in an amount sufficient so that said pH indicator composition is capable of exhibiting a color at a selected temperature below freezing, which color is the same as the color of said pH indicator composition at a temperature above freezing.

41. A temperature indicating device for use at sub-freezing temperatures comprising a sealed casing at least a portion of which is substantially translucent or transparent, said casing containing a thermochromic composition having controlled reversible change of color at a selected sub-freezing temperature, said composition comprising:

(A) at least one pH indicator in an amount sufficient to display a change of color upon change of pH;

(B) an aqueous buffer solution containing at least one inorganic ion in solution, wherein said buffer solution has a pH which is capable of changing when temperature of said buffer solution is lowered from a first temperature above the freezing point of said solution to a second temperature at which said solution is in a frozen state; and (C) a control agent or a precursor of a control agent, wherein said control agent is capable of effecting a change in ionic strength and proton composition of said pH indicator composition when frozen to thereby cause, upon freezing, a shift in change in pH of said pH indicator composition from that due to the pH change of said buffer solution;

and wherein said pH indicator has a pK value in said pH indicator composition and said control agent is in an effective amount to cause a change in said proton composition so that:

(a) for a pH indicator composition which becomes more acidic on freezing, said proton composition is changed to a value less than that at said pK value; and (b) for a pH indicator composition which becomes more alkaline on freezing, said proton composition is changed to a value greater than that at said pK value.

42. Device according to claim 41 wherein said casing is comprised of a material that is substantially impermeable to moisture at temperatures between about +25° and −90° C.

43. Device according to claim 41 wherein said casing is a substantially moisture impermeable, flexible, elongated tube comprised of a thermoplastic material mounted on a substantially rigid frame for said tube.

44. Device according to claim 41 wherein said casing is an elongated tube.

45. Device according to claim 44 wherein said elongated tube is comprised of glass or plastic.

46. Device according to claim 41 for indicating temperatures within a preselected range, wherein said casing is comprised of a multiplicity of discrete chambers, each chamber containing said thermochromic composition, such that the change of color exhibited by the contents of each of said chambers occurs at a selected sub-freezing temperature that is different from the sub-freezing temperature at which the contents of any other of said chambers exhibits a color change.

47. Device according to claim 46 wherein each of said chambers is comprised of a thermoplastic material.

48. Device according to claim 47 wherein said casing is in the shape of an elongated tube.

* * * * *